United States Patent [19]

Frijters et al.

[11] Patent Number: 4,513,685
[45] Date of Patent: Apr. 30, 1985

[54] METHOD AND DEVICE FOR RAISING WORMS, METHOD OF RAISING WORMS IN NUTRITION LIMITED BY INHIBITING MEANS, METHOD OF PRODUCING WORM CASTINGS, AND HOLDER FOR RAISING WORMS

[76] Inventors: Petrus J. G. Frijters, v.d. Duynstraat 152, 2515 NL The Hague; Antonie F. van Es, Maziestraat 18, 2514 GT The Hague, both of Netherlands

[21] Appl. No.: 480,375

[22] Filed: Mar. 30, 1983

[30] Foreign Application Priority Data

Apr. 7, 1982 [NL] Netherlands ................ 8201490

[51] Int. Cl.³ .............................................. A01K 67/00
[52] U.S. Cl. ..................................... 119/1; 119/15
[58] Field of Search ................................ 119/1, 15

[56] References Cited

U.S. PATENT DOCUMENTS

| | | | |
|---|---|---|---|
| 2,867,055 | 1/1959 | Lebiedzinski | 119/1 X |
| 3,566,836 | 3/1971 | Elfert | 119/1 |
| 3,635,816 | 1/1972 | Golub | 119/1 X |
| 3,654,903 | 4/1972 | Montgomery | 119/15 |
| 3,961,603 | 6/1976 | Gaddie, Sr. | 119/15 |
| 4,262,633 | 4/1981 | Taboga | 119/1 |

Primary Examiner—Hugh R. Chamblee
Attorney, Agent, or Firm—Birch, Stewart, Kolasch & Birch

[57] ABSTRACT

A method and a device are disclosed for raising worms. The worms are fed in accordance with a continuously growing nutritional chain in a manner such that a migration of a worm population following said chain is produced. At least once an accretion of the worm population is separated leaving a migrating stock population in the nutritional chain, whereas the accretion migrates in the direction of an accretion nutritional chain which starts from the stock nutritional chain, and can be harvested therefrom. Apparatus is described for raising the worms under conditions which are optimal for the farmer and depend, for instance, on economical and seasonal conditions.

The method and/or device can be advantageously used for producing worm casting, since the worms can be maintained under conditions whereby the conversion velocity of the nutrition offered to the worms is maximal over a long period of time.

26 Claims, 16 Drawing Figures

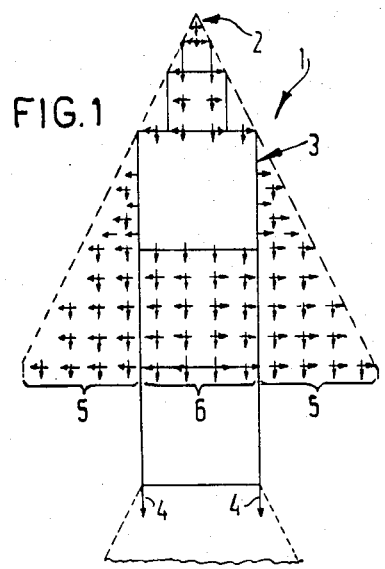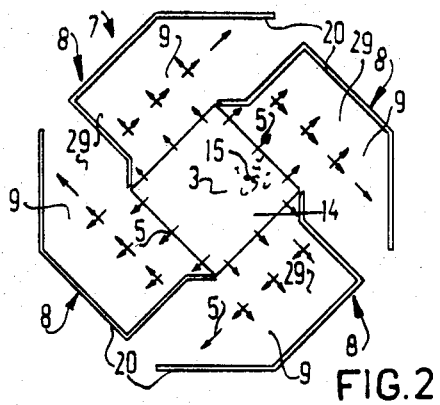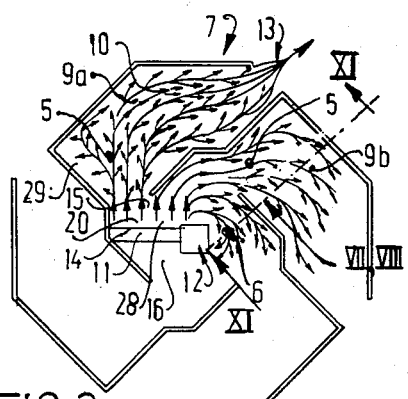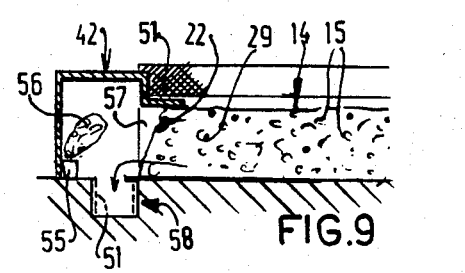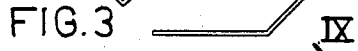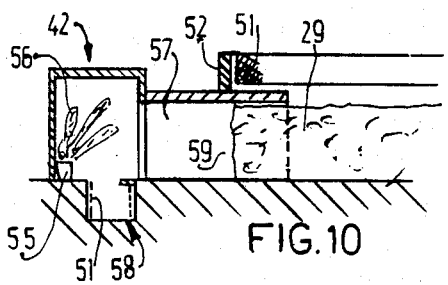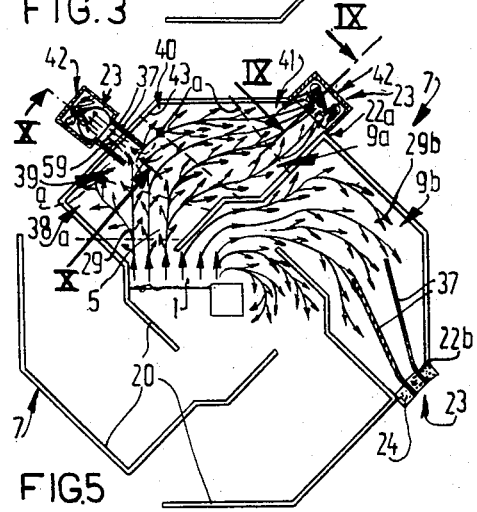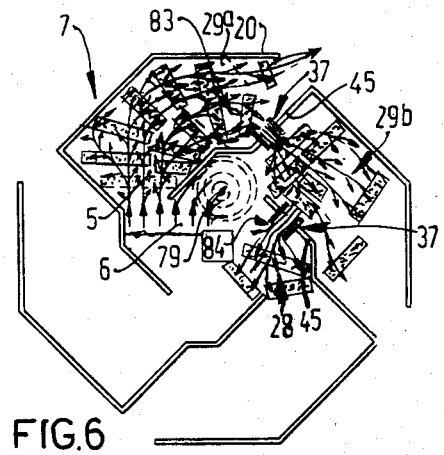

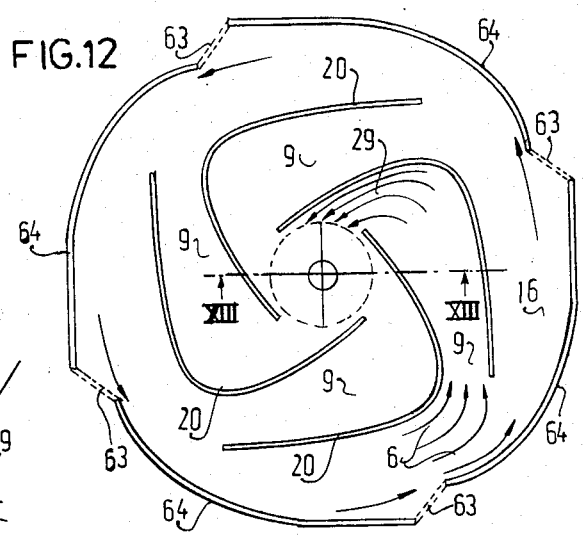
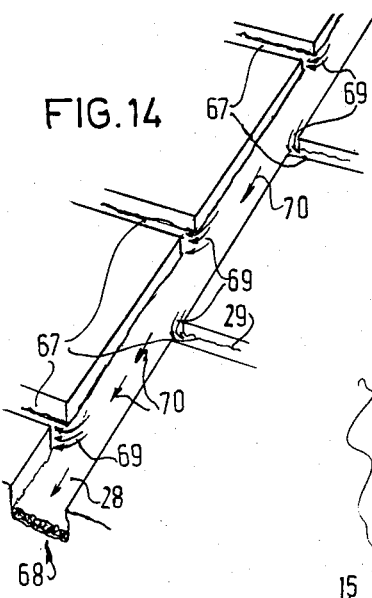
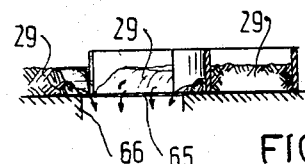
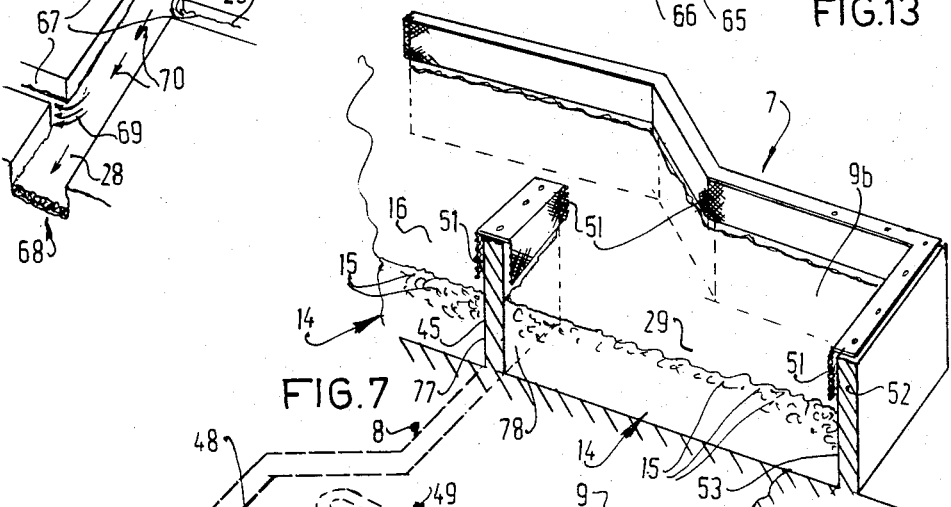
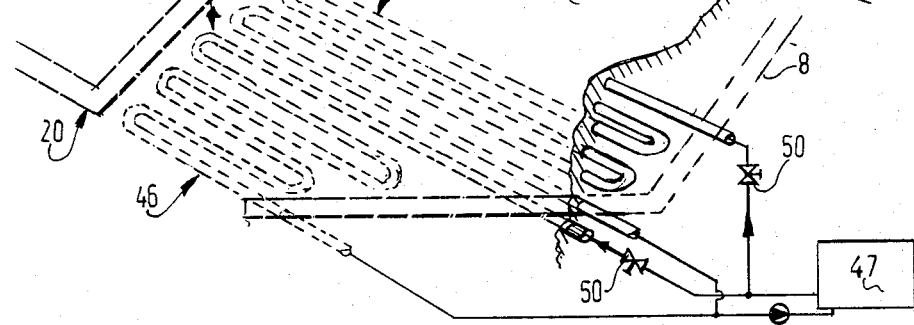

METHOD AND DEVICE FOR RAISING WORMS, METHOD OF RAISING WORMS IN NUTRITION LIMITED BY INHIBITING MEANS, METHOD OF PRODUCING WORM CASTINGS, AND HOLDER FOR RAISING WORMS

BACKGROUND OF THE INVENTION

The invention relates to a method for raising a worm population, in which nutrition is added to a worm population containing bedding, periodically accretion is separated from the worm population, and the remaining part of the worm population is maintained as a stock population.

Such a method is known from U.S. Pat. No. 3,961,603 which discloses a device for the cultivation of earth worms, which comprises a number of stacked pans which, with the exception of the bottom pan, are provided with orifices. The bottom pan is filled with gravel and water in order to maintain the relative humidity in the device at a constant level, whereas the uppermost pan is provided with a cover. The pans are so filled with bedding, that via the orifices the worms can travel from one pan to another and are always able to reach the nutrition which is added to the uppermost pan. Periodically the uppermost pan is removed and the worms, worm eggs, castings and bedding present therein, are separated from one another. Subsequently this pan is provided with fresh bedding and is replaced in the stack as the penultimate pan towards the bottom pan. Repeated harvesting of the worms from the converted nutrition and bedding is disadvantageous in that the job is labour intensive.

A similar method is described inter alia in the book "Raising Earthworms for Profit" by E. B. Shields (7th Edition, 1978, Shields Publications, Eagle River, Wis., U.S.A.). According to the known method a wooden or concrete trough, length 2.4 ms, width 90 cms and depth 30 to 40 cms is filled with bedding material. The bedding may consist of peat, horse-dung, straw, sawdust, wood mould and/or tree-bark and an important feature thereof is that it can contain water and has only little protein food. The bedding is stocked with such a concentration of worms that the worms can easily find one another and will reproduce. A trough of the abovementioned dimensions is stocked with about 100,000 worms. Suitable are, for example, earthworms such as Lumbricidae, Eiseniae, Allolobophorae, Dendrobaenae and the African night-crawler. After a period of ten days to one month the worms will seek food and come upwards. The nutrition is frequently deposited on the bedding and may be formed by organic refuse, dung, composte, sewerage mud, if necessary completed with commercially available food such as ground poultry fodder. After about two months the number of worms has doubled and the worm population has to be split up. For this purpose a further trough is half filled with bedding material and it is half filled of the worm-containing bedding from the first trough. Subsequently the remaining half of the initial trough is completed with new bedding material. This splitting-up process may be repeated about three times. After about six months the bedding of the initial trough contains such a large quantity of worm excrements that the worms living in this trough have to be separated from the bedding. Repeated splitting up the bedding in a trough containing a worm population has the disadvantage that the worms are disturbed, which adversely affects their behaviour. Additionally, gathering the worms from the worked-up nutrition and the bedding material is a labour-intensive process.

SUMMARY OF THE INVENTION

The method according to the invention overcomes the aforesaid disadvantages by adding to the bedding nutrition in accordance with a continuous growing nutritional chain in a manner such that a chain-following migration of a worm population is produced and by branching off an accretion at least once from a migrating worm population and by maintaining the remaining part of the worm population as a stock population in the nutritional chain. In this way the nutrition and bedding material processed by the worm population are continuously and automatically separated from this worm population by using the "new nutrition following" behavior of the worms to cause them to migrate in a direction desired by the raiser. Also the volume of the worm population reproducing during the migration is kept constant, since the accretion of worm population is gathered by separating it from the stock population.

Furthermore, maintaining a worm population at a constant, optimal density is advantageous because the reproduction velocity is high and the worms digest a maximum quantity of nutrition. This applies especially for young worms which in comparison with adult worms eat substantially more; all this leads to a relatively high conversion velocity of the offered nutrition and therefore to a relatively high production of worm castings.

Branching off the accretion is preferably carried out by adding nutrition to the growing nutritional chain and preferably by adding the nutrition producing branching of the accretion in accordance with a continuously growing accretion nutritional chain in a manner such that a migration following the accretion nutritional chain is brought about in the accretion.

In order to disturb the stock population as little as possible the stock population can be conducted so that the population need not be gathered for stocking a new bedding therewith. This is achieved by rendering the stock population self-inoculating and preferably in a sense such that the nutrition worked up by the stock population is conducted away and the nutrition for the stock population is added in accordance with a continuously growing stock nutritional chain such that a migration of the stock population is produced in endless manner. During the production of worms it may be desirable to decelerate or accelerate the migration of worms in dependence on supply and demand. This is preferably achieved by decelerating or accelerating the migration of the worms by building up the nutritional chain in a manner such that a surface area of a cross-section of the nutritional chain diverges or converges respectively in the direction of the growing nutritional chain. In the case of the accretion nutritional chain this is preferably achieved by an increase in the magnitude of the surface area of the cross-section of the accretion nutrional chain which sequentially diverges and converges and becomes a minimum at an end of the accretion nutritional chain remote from the stock nutritional chain.

Not only by changing the surface area of the cross-section of the nutritional chain but also by varying the environments of the nutritional chain the migration can be influenced. Means capable of varying the nutritional chain environments are added to the nutritional chain.

Such means for varying the nutritional chain environments are, for example, means locally varying the acidity after addition to the nutritional chain, means for applying voltage difference to the nutritional chain and means acting on the migration speed and the migration direction in a sense desired by the worm raiser by varying the temperature, the supply of food or by using the photophobic behaviour of worms by means of light.

If it is desired to cause at least a portion of the worm population contained in the nutritional chain to migrate from one place to another, which two places may be located in the same or in different nutritional chains, it is preferred to shortcircuit a distance of the migration of at least a portion of the population at one place in the nutritional chain by arranging guide means in the nutritional chain. These guide means may consist inter alia of stones or wooden walls forming a guide channel through which the portion of the worm population is guided to the other place under the influence of nutrition.

The accretion branched from the worm population may, if desired, be gathered in carrier material by arranging at the end of the accretion nutritional chain carrier material such as bags, attractive bedding material, for example, peat mould or precomposted cardboard, mixed as the case may be with some nutrition, the worms being received therein so that manipulations for separating worms from the bedding are not required. If it is desired to gather the worms without a carrier, it is preferred to harvest the worms by alluring them by odour out of the nutritional chain.

Prior to the removal of the accretion nutritional chain the remaining worms therein can be harvested by preferably increasing the temperature of the nutritional chain to a temperature which is unpleasant for the worms residing therein. In reaction the worms migrate to the uppermost layer of the accretion nutritional chain and by the removal of this uppermost layer the worms can be harvested in a relative high concentration and the remaining quantity of the accretion nutritional chain is substantially free of worms.

During the stay of the worms the biogas produced leaves the nutritional chain. Since the biogas produced is preferably captured by covering the nutritional chain with a biogas capturing member, the captured biogas may be employed for setting the temperature in the nutritional chain or it may be used for producing electricity which may be utilized by the means varying the nutritional chain environments. Moreover, by covering the nutritional chain odor nuisance is reduced.

The invention furthermore relates to a method of raising worms in a nutrition limited by inhibiting means. By the influence of a number of factors, for example, the air and nutrition humidity, the acidity and the supply of food, the worms may abruptly abandon the nutrition. If the inhibiting means comprise, as an inhibiting material, for example, concrete, wood, stone or the like the worms having abandoned the nutrition are frequently capable of escaping across the inhibiting means. The use of light to prevent the worms from escaping is usually very expensive due to the high costs of energy. The escape of worms can be avoided in a simple manner by fastening anti-creep means preferably at least to a part of the inhibiting means extending above the nutrition, the anti-creep means being for example a material preferably mosquito-netting having an air-pervious surface.

If desired, the nutrition of the worms may be organic refuse which is added so that the migration is brought about in a continuously growing organic refuse containing chain.

The invention furthermore relates to a method for producing worm castings wherein nutrition is converted into worm castings by the worms, the worms being raised according to the method of the invention. Since the worms are maintained in a optimal density according to these methods, the conversion velocity of the offered nutrition is relatively high and therefore the production of worm castings is also relatively high. Furthermore, the worms are maintained in controlled conditions and the quality of the offered nutrition can be determined before hand, so that the produced worm castings will have a good quality.

The invention relates to and provides a device for raising worms comprising at least one bedding and nutrition limited by inhibiting means in a worm-containing passage. Known devices have disadvantage that during the raising of the worms the accretion of the worm population cannot be separated out readily so that when the maximum worm density in the bedding or the nutrition is attained, the worms have to be separated from the bedding and the nutrition by the raiser, which is a labour-intensive and time-consuming job.

The invention has for its object to provide a device which is improved in this respect in that at least two passages are communicating with one another i.e. a stock passage containing a continuously growing stock nutritional chain and an accretion passage containing a continuously growing accretion nutritional chain.

Preferably the stock passage is formed by an endless passage, whilst the accretion passage communicates preferably through an outer wall of the stock passage with the stock passage.

When at least two accretion passages are communicating with one stock passage it is possible for the worms to migrate in one half of the stock passage and in one of the two accretion passages across the nutritional chains concerned, whereas through the other accretion passage the nutritional chain can be removed from the other part of the stock passage and from the accretion passage.

In the device embodying the invention preferably scaled accretion passages are arranged along the circumference and the inhibiting means preferably comprise a central core and at least two inhibiting elements arranged rotationally symmetrically with respect to the core and being spaced apart by equal angular intervals around the core. By this preferred design the device embodying the invention will occupy a minimum ground surface and have a most simple construction.

Under given conditions, for example a high degree of air humidity, the worms may abandon the nutrition and can escape over and across the inhibiting means from the device. The escape from the device is prevented by providing at least a portion of the inhibiting means extending above the nutrition with anti-creep means, which is preferably formed by a material having an air previous surface, for example, a mosquito netting.

A further preferred embodiment of the device according to the invention is characterized in that the passages are provided with means for adding means varying the nutrition environments, whilst if desired, guide means are arranged in the passages.

The migration of the worms in the direction of the growing nutritional chain is determined inter alia by the worm density in the nutritional chain. When in the direction of the migration the surface of a cross-section of the passage diverges, that is to say, with the same height of the nutritional chain the width of the nutritional chain increases, the worm will produce so that the migration velocity decreases. In the case of convergence of the surface of the cross-section of the passage in the direction of the migration the migration velocity of the worms increases. This variation in migration velocity in the device embodying the invention is obtained by the sequential divergence and convergence of the surface of a cross-section of the passage. After the accretion is branched from the stock population and the accretion population has reproduced, the accretion population of high density can be gathered at an end of the accretion passage remote from the stock passage preferably provided with a gathering opening, at which the surface of the cross-section of the accretion passage is at a minimum and to which gathering means are adjoined. The worms can be advantageously gathered by gathering means comprising bales of attractive bedding material disposed in the gathering opening in contact with the accretion nutritional chain so that the worms migrate into the bales. When the worms have to be gathered without carrier material, it is preferred to provied the gathering means with an odour trap.

BRIEF DESCRIPTION OF THE DRAWINGS

The above-mentioned and further features will be described more fully with reference to the drawings in which:

FIG. 1 is a diagrammatic representation of the principle of the method, and the device embodying the invention, FIG. 2 a plan view of a device embodying the invention, FIGS. 3, 5, 6, 12 and 15 are plan views of relatively different worm producing devices embodying the invention, FIG. 9 is an enlarged cross-sectional view taken on the line IX—IX in FIG. 5, FIG. 10 is an enlarged sectional view taken on the line X—X in FIG. 5, FIG. 11 an enlarged sectional view taken on the line XI—XI in FIG. 3 of a variant of the device embodying the invention, FIG. 13 a sectional view taken on the line XIII—XIII in FIG. 12, FIG. 14 is a perspective view of a variant of the device shown in FIG. 3.

FIG. 1 schematically shows a quadratically reproducing worm population 1, in which after inoculation 2 the population 1 grows into a population of a volume 3. In the direction of the arrows 4 an accretion 5 of the worm population 1 is branched and the remaining part of the worm population 1 is maintained as a stock population 6 of a volume 3. Branching of the accretion 5 can be continuously carried out.

FIG. 2 shows a device 7 for raising worms in accordance with the invention. In this device 7 the volume 3 is situated centrally and the accretion 5 leaves the volume 3 through inhibiting means 8 of the accretion passages 9.

Figure 4:
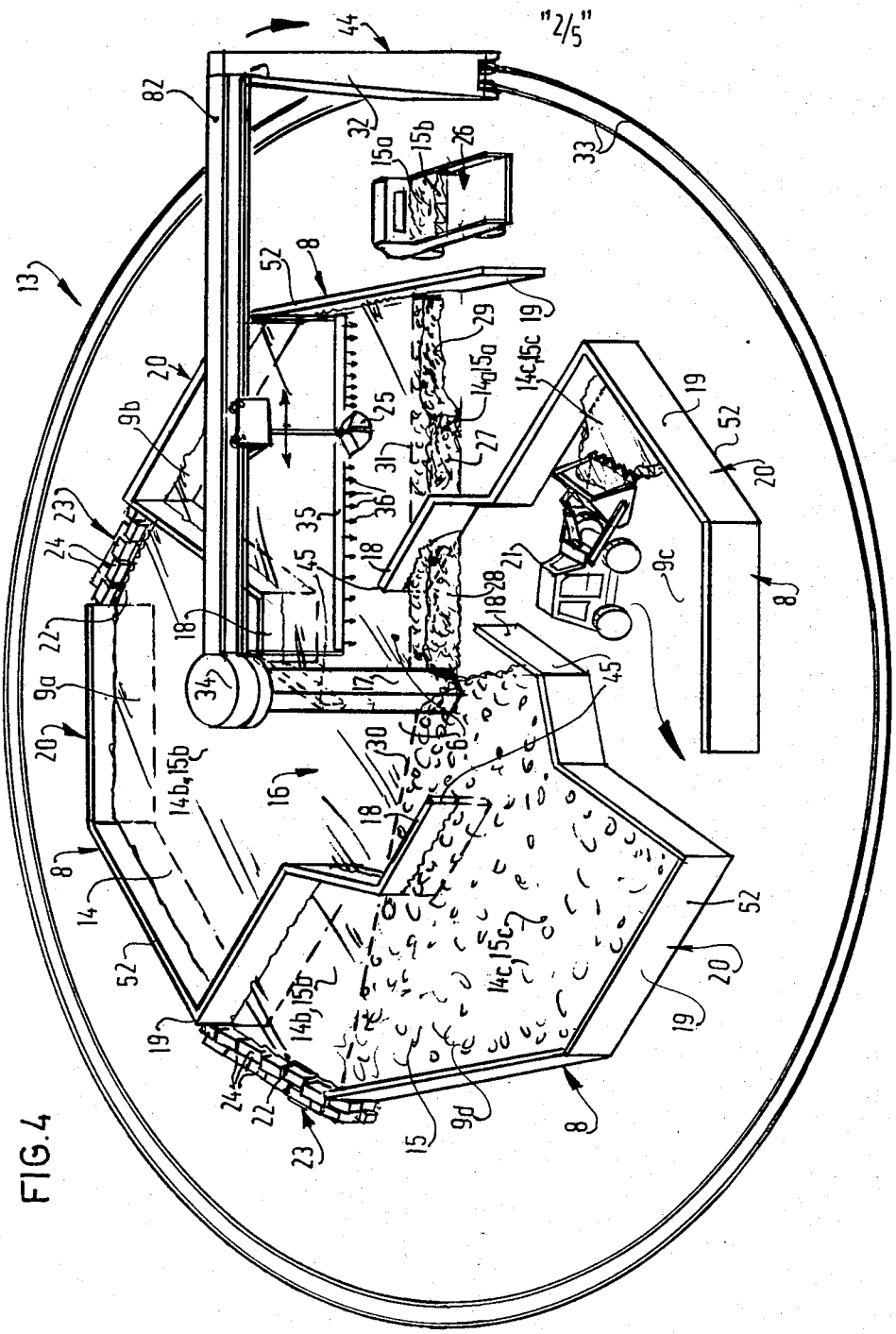
FIG. 4 is an enlarged, detailed view of the device of FIG. 3, FIGS. 7 and 8 are enlarged, perspective, fragmentary elevational views of a variant of detail VII and VIII respectively of FIG. 3.

In the device 7 of FIG. 2 the volume 3 is filled with a bedding 14 and a nutrition 15. Subsequently the bedding 14 is inoculated with worms. After the worm population has grown to a population of the volume 3, a continuously growing accretion nutritional chain 29 is added in each accretion passage 9 to the bedding 14 in a manner such that a migration of the worm population following the chain 29 is simultaneously produced in each accretion passage.

A plurality of devices 7 may be arranged side by side, whilst in order to obtain a continous production of accretions one of the devices 7 is inoculated, whereas gathering is carried out in a further device. A portion of the gathered worms may be used as inoculating worms in one device.

In the device 7 of FIG. 3 a central stock passage 16 is only partly filled with bedding material and after inoculation in an inoculation strip 11 the worms migrate in the direction to the nutrition added to the bedding 14. The nutrition 15 is added in accordance with continuously growing nutritional chains 28 and 29 in a manner such that the migrating accretion 5 in accordance with a continuously growing accretion nutritional chain 29 is separated from the worm population and the remaining portion of the population is maintained as a migrating stock population in an endless stock passage 16. If desired, the nutrition 15 may at least partly consist of bedding material. Thus the nutritional chain 28,29 may consist wholly or partly of nutrition 15.

After reproduction in an accretion passage 9a the accretion 5 leaves the device 7 beyond a gathering opening 13. A new accretion 5 is then again separated through a further accretion passage from the circulating stock population 6 and so on.

FIG. 4 shows a device 13 in operation in accordance with the invention. The device 13 comprises a bedding 14 limited by inhibiting means 8 and a nutrition 15 and worm receiving passages i.e. an endless stock passage 16 and four accretion passages 9a, 9b, 9c and 9d communicating with the stock passage 16. The accretion passages 9 are scaled and distributed along the circumference of the stock passage 16. The inhibiting means 8 limiting the passages 16 and 9 comprise a central core 17 and four inhibiting means 20 each formed by a portion 18 the outer wall 45 of the stock passage 16, by a further portion 19 and walls 52 of the accretion passage 9. These inhibiting means 20 are rotationally symmetrical to the core 17 and spaced apart by equal angular distances around the core 17.

In the device 13 a bulldozer 21 is used to remove the nutrition 15c and the bedding 14c abandoned by the worms from the stock passage 16 and the accretion passages 9c and 9d. Against the worm containing nutrition 15b and the bedding 14b in the accretion passages 9d and 9a are disposed in the gathering openings 22 gathering means 23 comprising bales of attractive bedding material 24 so that the worms migrating into the bales 24 can be gathered without nutrition 15b and without the bedding 14b.

By means of a loading crane 44 and a grabber 25 fresh nutrition 15a and fresh bedding material 14a delivered from a van are added in accordance with a continuously growing nutritional chain 27 in a manner such that a migration of a stock population 6 following a stock nutritional chain 28 in the stock passage 16 and a migration following an accretion nutritional chain 29 in the accretion passage 9b are produced. The line 30 indicates the separation between the nutrition 15c worked up and abandoned by the worms and the bedding 14c and the worm containing nutrition 15b and the bedding 14b. The line 31 indicates the separation between the worm containing nutrition 15b and the bedding 14b and the gresh, newly supplied nutrition 15a and the bedding 14a. During operation these lines 30 and 31 turn in the device 13 in clockwise direction around the core 17.

In order to supply fresh nutrition 15a and fresh bedding material 14a to the line 31 turning around the core 17 the loading crane 44 is, on the one hand, movable by a post 32 along the rails 33 around the device and on the other hand rotatable with a loading boom 82 on the top 34 of the core 17.

The loading crane 44 is provided with a sprinkling system 35 for supplying means such as water for varying the nutritional environment 36 of the nutrition 15 and the bedding 14.

FIG. 5 shows a device 7 in which guide means 37 are arranged in the passages 9a and 9b. After the area of separation of the accretion 5 from the worm population 1 the surface of the cross-section of the accretion nutritional chain 39 diverges towards the gathering opening 22a and the accretion 5 propagates in the sectors 38 and 39 of the accretion nutritional chain 29. Thereafter the surface of the cross-section a converges in the sectors 40 and 41 in the migration direction so that the reproduction speed decreases in the volume of the accretion nutritional chain 29 to be at a maximum at the gathering opening 22a. Around the gathering opening 22a is connected an odour trap 42 embraced by the gathering means 23 to harvest clean worms.

Through a sidewall 43 and guide means 37 an odour trap 42 is connected with the sector 39 of the accretion nutritional chain 29 and a specific age group of the accretion 5 can be gathered by opening the guide means 37 at the instant when the specific group of worms is passing by.

In the accretion nutritional chain 29b in the accretion passage 9b guide means 37 are arranged which guide a representative group of the accretion 5 towards the gathering opening 22b. This enable feeding this group in a different manner so that, for example, the colour of the group changes. In the gathering opening 22b are arranged bales of attractive bedding material 24.

Referring to FIG. 6 the guide means 37 are arranged across the wall 45 of the stock passage and the distance along which worms migrate from the accretion nutritional chain 29b to the stock nutritional chain 28 is shortcircuited. If necessary, by passing further guide means 37 through the wall 45 located between the accretion nutritional chain 29a and 29 b at least a portion of the accretion 5 can be guided back into the stock passage 6 over a distance bypassed by the guide means 37.

In the variant shown in FIG. 7 the accretion passage 9 is provided with tubes 46 surrounded by heat-exchanging means. The tubes 46 constitute circulating ducts 48 and 49, each of which communicates with a heat-exchanging unit 47. The circulating ducts 48 and 49 can each be closed by closing members 50 so that in sectors in the passage 9 the temperature in the accretion nutritional chain 29 can be set.

Of the wall 45 formed by the inhibiting means 8 between the stock passage 16 and the accretion wall 9a portion of the sidewalls 77 and 78, the portion extending above the nutrition 15 and the bedding 14 is provided with mosquitonetting 51. Of the outer wall 52 of the accretion passage 9 formed by the inhibiting means 8, only the portion of an inner surface 53 protruding above the nutrition 15 and the bedding 14 is provided with mosquito-netting 51.

Figure 8:
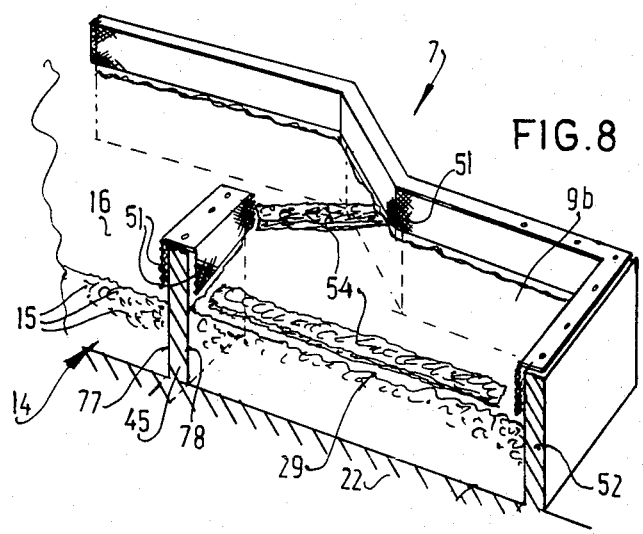

Referring to FIG. 8 nutrition strips 54 are disposed at intervals on the bedding 14 to form the nutritional chain 29. By constantly disposing new nutrition strips 54 in the direction towards the gathering opening 22 a migration of worms following the nutrition strips 54 towards the gathering opening 22 is produced.

Referring to FIG. 9, an odour trap 42 is connected in the gathering opening 22 with the accretion nutritional chain 29. In an odour generator 55 odorants 56 are produced, spreading in the space 57 of the odour trap 42. Under the influence of the odorants 56 the worms are allured out of the accretion nutritional chain 29 to cause them to move in the direction towards the odour generator 55, where they drop into the trap 58. In this way they are gathered without bedding 14 or nutrition 15.

As shown in FIG. 10 the odour trap 42 communicates through an opening 59 in the wall 52 with the accretion nutritional chain 29.

Figure 11:
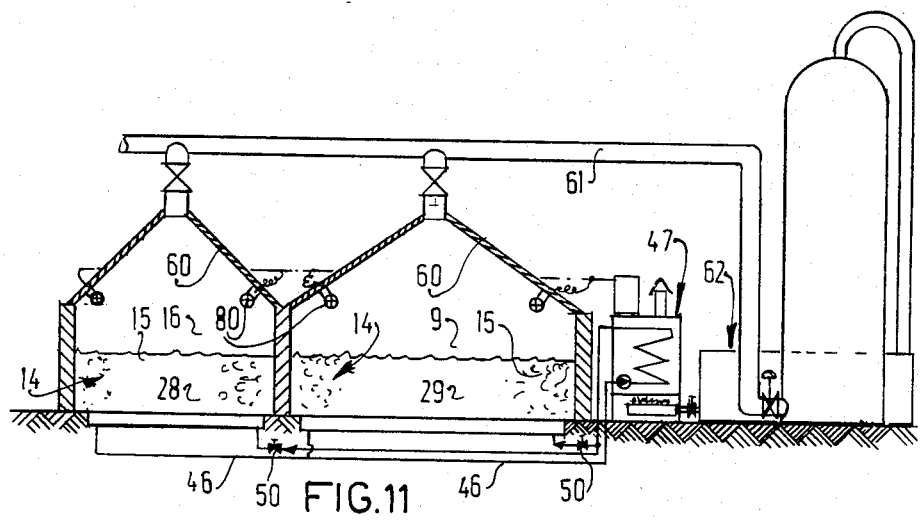

In the variant shown in FIG. 11 the accretion passage 9 and the stock passage 16 are each covered by a collector 60 for capturing biogas produced in the passages 9 and 16. The gas is guided through ducts 61 to a gas separator 62, where it is separated from air. The gas is used for generating energy and this energy is supplied to the heat-exchanging unit 47. By means of the heat-exchanging unit 47, in accordance with the situation represented in FIG. 7, the temperature in the nutritional chain 28 of the stock passage and in the accretion nutritional chain 29 can be set. Moreover, darkness prevails even by day in the covered passages 9 and 16. Therefore, the worms also feed by day on the nutrition 15 on the bedding 14, which results in a higher production of worms. Moreover, a lighting system 80 is provided in the passages 9 and 16.

In the variant of FIG. 12 the stock population 6 migrates in a stock passage 16 arranged around the accretion passages 9. The stock passage 16 and the accretion passages 9 are accessible for the bulldozer 21 trough opening 63 that can be closed. In this variant the inhibiting elements 20 and the outer wall portions 64 have a smooth shape.

Referring to FIG. 13, the worms of the accretion nutritional chains 29 are gathered by collecting them in a collecting tray 66 after having passed through a grid 65.

In the variant of FIG. 14 a number of accretion passages 67 communicate with a stock passage 68. Thus an accretion 69 can be continuously separated from the migrating stock population 70.

Figure 15:
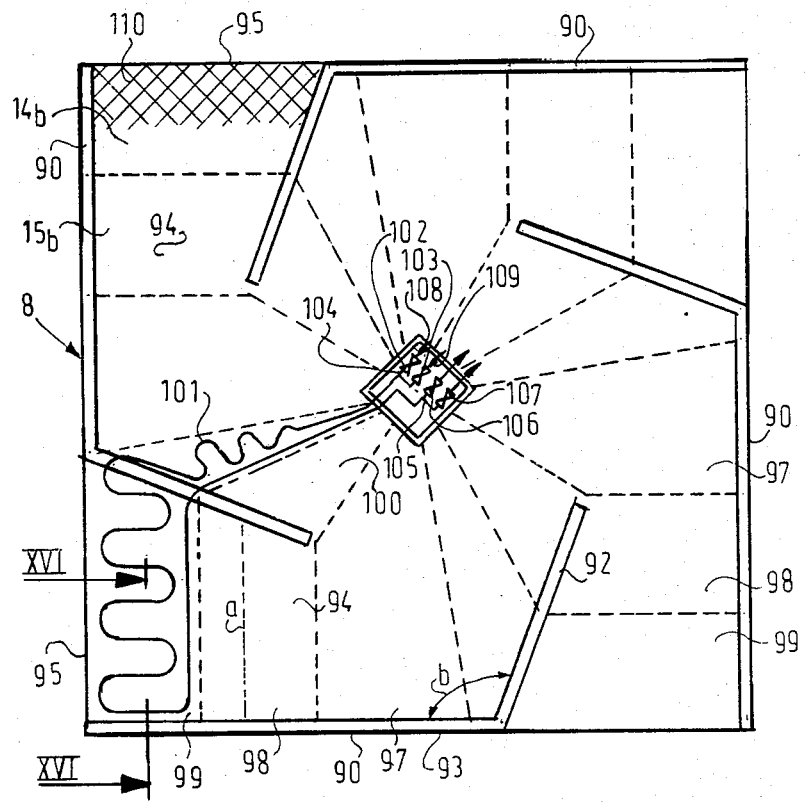

Referring to FIG. 15 the inhibiting means 8 comprise four inhibiting elements 90 which are rotation-symmetrical to the core 91 and spaced apart by equal angular distances around the core 91 and each include walls 92 and 93 which enclose an obtuse angle b. The surface of the cross-section a of the accretion passage 94 diverges towards the gathering opening 95.

The ground surface 96 is divided into four groups of three sectors 97,98,99 each, which comprise parts of the accretion passage 94 and the stock passage 100, which are adjacent to one another. Each sector 97 is provided with a channel 101 for feeding a fluid, which is fed via the valves 102 and 103 respectively, the manifold 104, the manifold 105 and the valves 106 and 107, respectively, as desired with a fluid 108 or a fluidum 109, with which the temperature of the nutrition chain 28,29 which is present in the sector 97, 98, 99 can be maintained at a optimal temperature for raising the worms (for instance about 30° C.), or at a temperature which is unpleasant for the worms residing therein (for instance about 40° C.).

In the gathering opening 95 a strip 110 of bedding 14b and nutrition 15b of material which is attractive for the worms, which material comprises for instance pre-composted cardboard, peat, applepulp and if necessary horse dung. By means of among other things the odour of this material the worms migrate into the strip 110. For instance weekly this strip 110 is removed and for instance using the "light fleeing attitude" of the worms, the worms can be harvested according to methods known in the art. Subsequently this material is replaced in the form of the strip 110 and juvenile worms which grew up in the meantime to adult worms can be taken up in this material, Accordingly during for instance three months worms can be harvested. It is also possible to use this material with the worms therein for starting another device.

Figure 16:
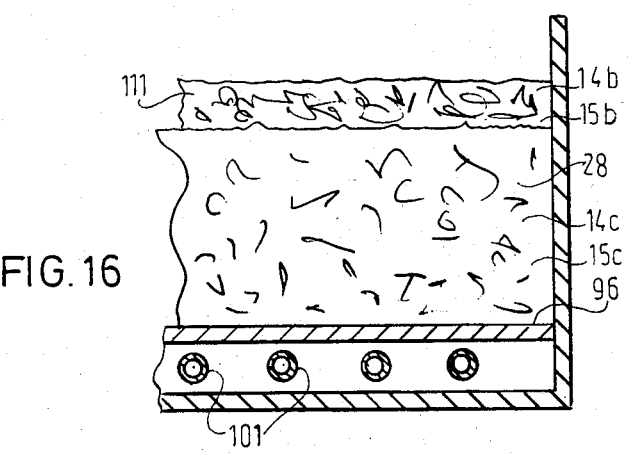
FIG. 16 is a sectional view taken on the line XVI—XVI.

Prior to the removal of the converted nutrition 15c and bedding 14c, which is converted into worm castings, the worms which are still present in the nutrition chain 28 can be harvested by feeding the channel 101 with the fluid 109, so that the temperature of the nutrition chain 28 is raised to a temperature which is unpleasant for the worms which reside therein. The worms migrate into the uppermost layer 111 which comprises nutrition 15b and bedding 14b. Subsequently the worms can be harvested by removing the layer 111 and in the accretion passage 94 remains a layer of worm castings which is substantially free of worms (FIG. 16).

What we claim is:

1. A method for raising and harvesting worms in a nutrition-containing bedding comprising:
   extending said bedding for defining a path by adding nutrition-containing material adjacent a portion of said bedding for inducing a worm population in said bedding to migrate along said path while said population is reproducing and increasing;
   directing an accretion portion of said migrating worm population into means for separating said accretion portion from said bedding; and p1 maintaining the remaining portion of said migrating worm population in said bedding as a stock population.

2. The method as claimed in claim 1, further comprising accelerating or decelerating the migration of the worm population by varying the area or cross-section of said path.

3. The method as claimed in claim 1, further comprising controlling the temperature in the bedding to maintain different temperatures in different sectors of the bedding.

4. The method as claimed in claim 1, further comprising gathering the worms by directing said accretion portion of the population into a carrier material which comprises a second bedding material.

5. The method as claimed in claim 1, further comprising gathering the worms by alluring the accretion portion of the population by means of an odour.

6. The method as claimed in claim 1, further comprising gathering the worms by increasing the temperature of a part of the bedding to a temperature which is unpleasant for the worms residing therein for inducing the worms toward a collection region of different temperature.

7. The method as claimed in claim 1, wherein the nutrition is organic refuse.

8. The method of claim 1 wherein nutrition-containing bedding is converted into worm castings by the worm population and the worm castings are removed after the worms have migrated therefrom.

9. The method of claim 1, further comprising removing exhausted portions of said bedding from which the nutrition has been depleted by said migrating worm population.

10. The method of claim 1, further comprising removing exhausted portions of said bedding from which the nutrition has been depleted by said migrating worm population, and replacing at least a part of said exhausted portions for defining an endless migration path for said stock population.

11. The method as claimed in claim 1, further comprising influencing the worm migration by varying the environment of the bedding.

12. The method of claim 11, comprising varying the environment of said bedding by adding substances thereto.

13. Apparatus for raising worms comprising means for supporting a nutrition-containing bedding and at least one divider means for defining at least two passages through said bedding in communication with one another, at least a first passage defining a stock passage for containing a stock population of worms and at least a second passage defining an accretion passage for containing a continuously growing migration of an accretion population of worms.

14. The apparatus as claimed in claim 13, wherein the stock passage has a configuration which permits an endless migration loop for said stock population.

15. The apparatus as claimed in claim 13, further comprising means for varying the environment in said nutrition-containing bedding within said passages.

16. The apparatus as claimed in claim 13, further comprising guide means within said accretion passage along at least a portion of the path of migration of the accretion population of worms.

17. The apparatus as claimed in claim 13, further comprising a collector covering said device for capturing produced biogas.

18. The apparatus as claimed in claim 13 comprising at least two accretion passages communicating with one stock passage through said at least one divider means.

19. The apparatus as claimed in claim 18, wherein the accretion passages are positioned about the circumference of the stock passage.

20. The apparatus as claimed in claim 19, comprising a central core and at least two divider means arranged at equal angular intervals around the core for defining said passages.

21. The apparatus as claimed in claim 13, wherein the cross-section of the accretion passage varies over at least a part of the accretion passage.

22. The apparatus of claim 21, further comprising a worm gathering opening at an end portion of said accretion passage.

23. The apparatus as claimed in claim 22, further comprising gathering means connected with the worm gathering opening for receiving the worms.

24. The apparatus of claim 23, wherein said worm gathering means comprises a mass of carrier material or an odor trap.

25. The apparatus as claimed in claim 13, further comprising heat-exchanging means for varying the temperature of at least a portion of said nutrition-containing bedding.

26. The apparatus of claim 25, wherein said heat exchanging means comprises means for carrying a heat exchanging fluid below said means for supporting said bedding.

* * * * *